(12) United States Patent
Huang et al.

(10) Patent No.: US 12,378,563 B2
(45) Date of Patent: Aug. 5, 2025

(54) METHOD FOR PREPARING IMMOBILIZED ARGININE DEIMINASE (ADI) AND PRODUCING [$^{14/15}$N]-L-CITRULLINE

(71) Applicant: SHANGHAI UNIVERSITY OF MEDICINE&HEALTH SCIENCES, Shanghai (CN)

(72) Inventors: Gang Huang, Shanghai (CN); Bin Li, Shanghai (CN); Yue Li, Shanghai (CN)

(73) Assignee: SHANGHAI UNIVERSITY OF MEDICINE & HEALTH SCIENCES, Shanghai (CN)

( * ) Notice: Subject to any disclaimer, the term of this patent is extended or adjusted under 35 U.S.C. 154(b) by 0 days.

(21) Appl. No.: 17/766,738

(22) PCT Filed: Oct. 13, 2020

(86) PCT No.: PCT/CN2020/120719
§ 371 (c)(1),
(2) Date: Apr. 6, 2022

(87) PCT Pub. No.: WO2021/088603
PCT Pub. Date: May 14, 2021

(65) Prior Publication Data
US 2023/0132468 A1    May 4, 2023

(30) Foreign Application Priority Data

Nov. 6, 2019 (CN) .......................... 201911078370.6
Apr. 23, 2020 (CN) .......................... 202010328248.6

(51) Int. Cl.
| | | |
|---|---|---|
| *C12N 15/77* | (2006.01) | |
| *C12N 1/00* | (2006.01) | |
| *C12N 1/20* | (2006.01) | |
| *C12N 9/78* | (2006.01) | |
| *C12N 15/66* | (2006.01) | |
| *C12P 13/10* | (2006.01) | |
| *C12R 1/15* | (2006.01) | |

(52) U.S. Cl.
CPC ............ *C12N 15/77* (2013.01); *C12N 1/005* (2013.01); *C12N 1/20* (2013.01); *C12N 9/78* (2013.01); *C12N 15/66* (2013.01); *C12P 13/10* (2013.01); *C12Y 305/03006* (2013.01); *C07K 2319/735* (2013.01); *C12R 2001/15* (2021.05)

(58) Field of Classification Search
CPC . C12N 9/78; C12N 15/77; C12N 1/20; C12N 15/66; C12P 13/10; C12Y 305/03006; C07K 2319/735; C07K 2319/73; C12R 2001/15
See application file for complete search history.

(56) References Cited

FOREIGN PATENT DOCUMENTS

| | | | | |
|---|---|---|---|---|
| CN | 101993867 A | | 3/2011 | |
| CN | 104805144 A | | 7/2015 | |
| CN | 105483060 A | | 4/2016 | |
| CN | 110563852 A | * | 12/2019 | ............ C07K 14/28 |
| EP | 3330282 A1 | * | 6/2018 | ............ C07K 14/24 |
| KR | 2006026082 A | * | 3/2006 | ............ A23C 9/123 |
| WO | 2014138319 A2 | | 9/2014 | |

OTHER PUBLICATIONS

English translation of CN 110563852 A. (Year: 2019).*
English translation of KR 2006026082 A (Year: 2006).*
Singh et al. "Protein recovery from inclusion bodies of *Escherichia coli* using mild solubilization process", 2015, Microbial Cell Factories, vol. 14, Article 41, p. 1-10. (Year: 2015).*
Jung Kirsten, et al., CipA, CipB and Pixa as Scaffolds to Organize Proteins Into Crystalline Inclusions, EP Patent Application, EP20160202046, 2016, pp. 1-53. (Year: 2016).*
Wang, et al., CipA and CipB as Scaffolds To Organize Proteins into Crystalline Inclusions, ACS Synthetic Biology, 2017, pp. 826-836, vol. 6, No. 5. (Year: 2017).*
Bintrim et al. "Insertional Inactivation of Genes Encoding the Crystalline Inclusion Proteins of Photorhabdus luminescens Results in Mutants with Pleiotropic Phenotypes", Mar. 1998, Journal of Bacteriology, vol. 180, Issue 5, p. 1261-1269. (Year: 1998).*
Chen et al. "A novel protein purification strategy mediated by the combination of CipA and Ssp DnaB intein", Jun. 7, 2019, Journal of Biotechnology, vol. 301, p. 97-104. (Year: 2019).*
Huo et al. "CipA-mediating enzyme self-assembly to enhance the biosynthesis of pyrogallol in *Escherichia coli*" Sep. 22, 2018, Applied Microbiology and Biotechnology, vol. 102, p. 10005-10015. (Year: 2018).*
Jong-Eun Kim, et al., Expression, purification, and characterization of arginine deiminase from *Lactococcus lactis* ssp. *lactis* ATCC 7962 in *Escherichia coli* BL21, Protein Expression and Purification, 2007, pp. 9-15, vol. 53. (Year: 2007).*
Liu et al. "Removal of Endotoxin from Recombinant Protein Preparations", Aug. 1997, Clinical Biochemistry, vol. 30 Issue 6, pp. 455-463 (Year: 1997).*
Song et al. "Enzymatic production of l-citrulline by hydrolysis of the guanidinium group of l-arginine with recombinant arginine deiminase", May 27, 2015, Journal of Biotechnology, vol. 208, p. 37-43. (Year: 2008).*
Yang Wang, et al., CipA and CipB as Scaffolds To Organize Proteins into Crystalline Inclusions, ACS Synthetic Biology, 2017, pp. 826-836, vol. 6, No. 5.

(Continued)

Primary Examiner — Gary B Nickol
Assistant Examiner — Amelia Nicole Dickens
(74) Attorney, Agent, or Firm — Bayramoglu Law Offices LLC

(57) ABSTRACT

Arginine deiminase (ADI)-containing genetically engineered *Corynebacterium glutamicum* (*C. glutamicum*), a fusion protein cipA-arc, use thereof, and a method for preparing [$^{14/15}$N]-L-citrulline through enzymatic catalysis are provided. The ADI-containing genetically engineered *Corynebacterium glutamicum* (*C. glutamicum*) has a deposit number of CGMCC No. 19404, which expresses a fusion protein cipA-arc. Both the genetically engineered strain and the fusion protein cipA-arc can be used to convert [$^{14/15}$N]-L-arginine into [$^{14/15}$N]-L-citrulline.

17 Claims, No Drawings
Specification includes a Sequence Listing.

(56) References Cited

OTHER PUBLICATIONS

Jong-Eun Kim, et al., Expression, purification, and characterization of arginine deiminase from *Lactococcus lactis* ssp. *lactis* ATCC 7962 in *Escherichia coli* BL21, Protein Expression and Purification, 2007, pp. 9-15, vol. 53.
Jung Kirsten, et al., CipA, CipB and Pixa as Scaffolds to Organize Proteins Into Crystalline Inclusions, EP Patent Application, EP20160202046, 2016, pp. 1-53, this is a foreign patent application.
Ma Yue, et al., Optimization of Preparing L-citrulline by Recombinant Arginine Deiminase, Biotechnology Bulletin, 2015, pp. 180-185, vol. 31, No. 8.
Bintrim S.B., et al., AAA27616, crystalline inclusion protein type II [*Photorhabdus luminescens* subsp. *luminescens*], GenBank, 2001.
Kim J.E., et al., ABC88383, arginine deiminase [*Lactococcus lactis* subsp. *lactis*], GenBank, 2007.
Xue Cai, et al., Thermostability and Specific-Activity Enhancement of an Arginine Deiminase from Enterococcus faecalis SK23.001 via Semirational Design for L-Citrulline Production, Journal of Agricultural and Food Chemistry, 2018, pp. 8841-8850, vol. 66.

\* cited by examiner

METHOD FOR PREPARING IMMOBILIZED ARGININE DEIMINASE (ADI) AND PRODUCING [$^{14/15}$N]-L-CITRULLINE

CROSS REFERENCE TO THE RELATED APPLICATIONS

This application is the national phase entry of International Application No. PCT/CN2020/120719, filed on Oct. 13, 2020, which is based upon and claims priority to Chinese Patent Application No. 201911078370.6, filed on Nov. 6, 2019, and Chinese Patent Application No. 202010328248.6, filed on Apr. 23, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBDS001-PKG Sequence Listing.txt, created on Oct. 3, 2023, and is 2,819 bytes in size.

TECHNICAL FIELD

The present application relates to a method for preparing [$^{14/15}$N]-L-citrulline through biocatalysis, and belongs to the technical fields of biopharmaceuticals and biochemical engineering.

BACKGROUND

Citrulline is an alpha-amino acid, which was first obtained from watermelon and named thereby. L-citrulline can increase a level of nitric oxide in the human body, and nitric oxide can soothe the arteries and promote the systemic blood flow, thereby allowing the human body to well work. Citrulline shows obvious effects on the prevention and treatment of prostate diseases, such as prostatitis, prostate swelling, prostatic hypertrophy, and the like. Recent studies have shown that citrulline can be converted into an essential amino acid L-arginine in the human body. Arginine deficiency may lead to a range of cardiovascular diseases (CVDs), such as hypertension, atherosclerosis and heart failure. As a precursor for the synthesis of L-arginine, L-citrulline can be converted into L-arginine in many tissues, is not metabolized in the gastrointestinal tract and liver, and does not induce an increase in the activity of arginase. Therefore, L-citrulline supplementation can assist in the treatment of arginine deficiency-associated diseases. Citrulline shows high oxidation resistance, can scavenge free radicals, and can effectively protect DNA from oxidative reactions. Therefore, citrulline can be used as an anti-aging and immunity-enhancing health care product, and can also be used as a cosmetic with skin care, anti-wrinkle, and freckle removal effects. The administration of citrulline can effectively improve the body's anti-fatigue ability, maintain normal heart and lung functions, improve mental clarity, reduce stress and overcome depression, balance a blood glucose level, and enhance the body's muscle strength, which plays an important role in sports health.

At present, common production methods of citrulline mainly include a chemical synthesis process, an extraction process, a fermentation process, an enzymatic conversion process, and the like. The chemical synthesis process refers to hydrolyzing arginine under an alkaline condition to obtain citrulline. It is hard to control the process accurately, a product has non-single configurations and includes D-citrulline that affects a quality, and generated wastewater affects the environment. In patent CN105483060, citrulline is produced through fermentation, where mutation breeding is mainly adopted. It is difficult to obtain a high-yield strain due to the large randomness of strain production. This process has disadvantages such as low citrulline content in a natural product, limited raw material sources, small production scale, complicated process, and low yield. In patent CN104805144, the enzymatic conversion process is adopted to synthesize citrulline, which is simple. However, *Escherichia coli* (*E. coli*) is adopted, and *E. coli* includes endotoxin, a common disadvantage of Gram-negative bacteria (GNB), which limits the application in foods or cosmetics.

Preparation methods of immobilized enzymes are divided into two categories: physical methods and chemical methods. The physical methods include physical adsorption, embedding, and the like. An advantage of the physical method for immobilizing enzymes is that the enzymes do not participate in a chemical reaction, the overall structure thereof remains unchanged, and the catalytic activity of the enzymes is well retained. However, because an embedded material or a semipermeable membrane shows some steric hindrance, the embedding method is not suitable for some reactions. The chemical methods include binding and cross-linking. In the chemical methods, an enzyme is tightly bound to a carrier and is not easy to fall off, leading to high stability, but there are intense reaction conditions, complicated operations, harsh control conditions, and large activity loss.

SUMMARY

According to a first aspect of the present application, an arginine deiminase (ADI)-containing genetically engineered strain is provided, and the ADI is expressed in the genetically engineered strain. Specifically, the genetically engineered strain is *Corynebacterium glutamicum* (*C. glutamicum*), with a deposition name of *C. glutamicum* SUMHS-2020.01; the ADI is expressed in the *C. glutamicum*; and the genetically engineered strain was deposited in the China General Microbiological Culture Collection Center (CGMCC) of Chinese Academy of Sciences, No. 1, Beichen West Road, Chaoyang District, Beijing, China on Jan. 17, 2020, with a deposit number of CGMCC No. 19404.

The genetically engineered strain may be constructed by the following process:

introducing a HindIII site at a 5' terminus of a cipA gene sequence and introducing a SalI site at a 3' terminus of the cipA gene sequence to obtain a target fragment with a gene sequence of SEQ ID NO: 1, and sequencing the target fragment; subjecting each of the target fragment and an expression vector pXMJ19 to double enzyme digestion with HindIII/SalI, recovering each of enzyme digestion products by gel, and ligating the target fragment and the vector; and transforming a ligation product into *E. coli* DH5α competent cells to obtain a positive transformant pXMJ19-cipA; and introducing a XhoI site at a 5' terminus of an ADI arc gene sequence and introducing a SacI site at a 3' terminus of the ADI arc gene sequence to obtain a target fragment with a gene sequence of SEQ ID NO: 2, and sequencing the target fragment; subjecting each of the target fragment and the expression vector pXMJ19-cipA to double enzyme digestion with XhoI/SacI, recovering each of enzyme digestion products by gel, and ligating the target fragment and the vector; and transforming a ligation product into *E. coli* DH5α competent cells to obtain a positive transformant recombinant plasmid pXMJ19-cipA-arc.

According to a second aspect of the present application, a use of the ADI-containing genetically engineered strain according to the first aspect of the present application in the conversion of [$^{14/15}$N]-L-arginine to produce [$^{14/15}$N]-L-citrulline is provided.

According to a third aspect of the present application, a fusion protein cipA-arc is provided, where ADI arc is immobilized on an inclusion body cipA to produce an inclusion body cipA-arc with catalytic activity, which is the fusion protein cipA-arc.

Optionally, the fusion protein cipA-arc may be prepared through the following steps preparing *C. glutamicum* competent cells;

transforming the recombinant plasmid pXMJ19-cipA-arc into the *C. glutamicum* competent cells through electric shock; and subjecting the genetically engineered strain to induction expression to obtain recombinant whole cells, and subjecting the recombinant whole cells to ultrasonic disruption and centrifugation to obtain a precipitate, which is the fusion protein cipA-arc (that is, a form of the inclusion body cipA-arc is immobilized).

Optionally, the *C. glutamicum* competent cells may be prepared by the following process:

cultivating *C. glutamicum* ATCC13032 on an LBG-containing solid medium, picking and inoculating fresh bacteria in an LBG liquid medium, and cultivating; transferring an activated bacterial solution to an LBG medium at an inoculum amount of 0.8% to 1.5%, and continuing to cultivate until $OD_{600}$ is 0.8 to 1.0; pre-cooling a resulting bacterial solution by an ice/water mixture, centrifuging, and discarding a resulting supernatant; adding glycerin, and pipetting up and down until bacteria are suspended; centrifuging, and discarding a resulting supernatant; and adding glycerin, and pipetting up and down until the bacteria are suspended to obtain the *C. glutamicum* competent cells.

Preferably, *C. glutamicum* ATCC13032 is streaked on an LBG-containing solid medium plate (LBG liquid medium: 10 g of peptone, 5 g of yeast extract, 10 g of NaCl, and 5 g of glucose are mixed, a pH is adjusted to 7.0 to 7.5, and deionized water is added to 1 L; and solid medium plate: LBG liquid medium+12 g/L to 15 g/L agar powder) and cultivated in an incubator for a period of time; fresh bacteria are picked and inoculated in an LBG liquid medium, and cultivated for 12 h to 24 h in a shaker with a temperature of 20° C. to 40° C. and a rotational speed of 150 r/min to 300 r/min; an activated bacterial solution is transferred to an LBG medium at an inoculum amount of 1%, and cultivated in a shaker with a temperature of 20° C. to 40° C. and a rotational speed of 150 r/min to 300 r/min until $OD_{600}$ is 0.9; a resulting bacterial solution is pre-cooled for 15 min to 20 min in an ice/water mixture, then dispensed into sterilized centrifuge tubes in a clean bench, centrifuged at 6,000 g and 4° C. for 30 s, and placed in ice water for 2 min; a resulting supernatant in each centrifuge tube is discarded, pre-cooled 10% glycerin is added to each centrifuge tube, and a resulting mixture is slowly pipetted up and down with a pipette until bacteria are suspended; and a resulting suspension is centrifuged at 6,000 g and 4° C. for 30 s, a resulting supernatant is discarded, pre-cooled 10% glycerin is added, and a resulting mixture is slowly pipetted up and down until the bacteria are suspended.

Optionally, the cultivation each time may be conducted at a temperature of 30° C. and a rotational speed of 200 r/min.

Optionally, the recombinant plasmid pXMJ19-cipA-arc may be transformed into the competent cells through electric shock by the following process:

thoroughly mixing the *C. glutamicum* competent cells and the recombinant plasmid pXMJ19-cipA-arc, cooling a resulting mixture on ice, and subjecting the resulting mixture to electric shock for 1 ms to 10 ms at a voltage of 1 kV to 5 kV under the same temperature condition; adding an LBG liquid medium at room temperature, transferring a resulting mixture to a centrifuge tube, and subjecting the resulting mixture to shaking cultivation; coating a resulting bacterial solution on a chloramphenicol-resistant plate, and picking single colonies to extract the plasmid; confirming the insertion of the target fragment through double enzyme digestion and polymerase chain reaction (PCR); and inoculating an obtained recombinant strain.

Preferably, the *C. glutamicum* competent cells and the recombinant plasmid pXMJ19-cipA-arc are thoroughly mixed, cooled on ice for 10 min, and immediately added to an ice-cold cuvette, and electric shock is conducted for 3 ms to 7 ms at a voltage of 2 kV to 4 kV; the cuvette is taken out as soon as possible at the end of a pulse, an LBG liquid medium is added at room temperature, and a resulting mixture is transferred to a centrifuge tube and cultivated under gentle shaking for 2 b; a resulting bacterial solution is coated on a 20 µg/ml chloramphenicol-resistant plate; and single colonies are picked to extract the plasmid, and the insertion of the target fragment is confirmed through double enzyme digestion and PCR.

Optionally, the electric shock may be conducted at a voltage of 2.5 kV for 5 ms.

Optionally, a method of the induction expression of the genetically engineered strain may include:

inoculating the recombinant strain into a chloramphenicol-containing LBG medium, cultivating on a shaker until an $OD_{600}$ value of a bacterial solution reaches 0.8 to 1.0, and adding isopropyl-β-D-thiogalactoside (IPTG) to induce overnight; centrifuging to collect the recombinant whole cells, washing the recombinant whole cells with a Tris-HCl buffer, and resuspending the recombinant whole cells in phosphate buffer saline (PBS); and subjecting the recombinant whole cells to ultrasonic disruption, and centrifuging to obtain a precipitate, which is the fusion protein cipA-arc.

Preferably, the recombinant strain identified as positive is inoculated in an LBG medium that includes chloramphenicol at a final concentration of 20 ng/ml, and cultivated in a shaker with a temperature of 20° C. to 40° C. and a rotational speed of 150 r/min to 300 r/min until an $OD_{600}$ value of a bacterial solution reaches 0.9; IPTG is added at a final concentration of 1 mM to induce overnight at a temperature of 20° C. to 40° C. and a rotational speed of 150 r/min to 300 r/min, and a resulting bacterial solution is centrifuged at 4° C. to obtain the recombinant whole cells; and the recombinant whole cells are washed with a Tris-HCl buffer, resuspended in PBS, subjected to ultrasonic disruption, and centrifuged at 4° C. to obtain a precipitate, which is the fusion protein cipA-arc.

Optionally, the cultivation and the induction may be both conducted at 30° C.; the cultivation may be conducted at a rotational speed of 200 r/min; and the induction may be conducted at a rotational speed of 180 r/min.

Preferably, the Tris-HCl buffer may have a pH of 7.0.

Preferably, the PBS may have a pH of 6.5.

According to a fourth aspect of the present application, a use of the inclusion body cipA-arc (namely, the fusion protein cipA-arc) according to the third aspect of the present application in the conversion of [$^{14/15}$N]-L-arginine to produce [$^{14/15}$N]-L-citrulline is provided.

According to a fifth aspect of the present application, a method for preparing [$^{14/15}$N]-L-citrulline through enzymatic catalysis is provided, including the following step:
  adding the fusion protein cipA-arc (namely, the inclusion body cipA-arc) according to the third aspect of the present application to a conversion solution to allow a conversion reaction,
  where the conversion solution includes [$^{14/15}$N]-L-arginine and a buffer, and the conversion reaction is conducted for 2 h to 8 h at a temperature of 25° C. to 50° C. and a pH of 5.0 to 8.0.

Optionally, the buffer may be PBS; and the conversion reaction may be conducted for 5 h at a temperature of 37° C. and a pH of 6.0.

Optionally, the preparation method may further include: centrifuging to obtain a supernatant and a precipitate.

Optionally, the supernatant may be used to purify [$^{14/15}$N]-L-citrulline;
  a buffer may be added to the precipitate for resuspending, and a resulting suspension may be added to the conversion solution for conversion;
  preferably, the buffer may be PBS; and
  preferably, the PBS may have a pH of 6.0.

In the present application, the "cipA gene sequence" refers to the cipA gene sequence reported by Kirsten Jung et al. (Wang Y, Heermann R, Jung K. CipA and CipB as Scaffolds To Organize Proteins into Crystalline Inclusions [J]. ACS Synthetic Biology, 2017, 6, 826-836).

In the present application, the "arc gene sequence" refers to the ADI (arcA) gene sequence reported by Kim et al. (Kim J E, Jeong D W, Lee H J. Expression, purification, and characterization of arginine deiminase from *Lactococcus lactis* ssp. *lactis* ATCC 7962 in *Escherichia coli* BL21 [J]. Protein Expression and Purification, 2007, 53 (1): 0-15).

In the present application, the "pXMJ19" refers to a vector carrying a protein-expressing gene in *C. glutamicum*.

Possible beneficial effects of the present application:

In the present application, a gene of ADI is synthesized and cloned, and a genetically engineered strain with high ADI yield is constructed to express ADI in *C. glutamicum*.

In the present application, ADI is immobilized on an inclusion body cipA to produce an inclusion body cipA-arc (namely, a fusion protein cipA-arc) with catalytic activity.

The immobilized fusion protein cipA-ADI (cipA-arc) with catalytic activity provided in the present application can be used repeatedly for 50 times or more.

The inclusion body cipA-arc provided in the present application, namely, the immobilized fusion protein arc-cipA, can catalyze the conversion of [$^{14/15}$N]-L-arginine to produce [$^{14/15}$N]-L-citrulline, where a post-treatment is simple, a product is easily separated and purified, a cost is low, and the scale-up production is easy to achieve, which provides a new way for the enzymatic preparation of [$^{14/15}$N]-L-citrulline; and a resulting reaction solution can be subjected to vacuum concentration, crystallization, and drying to obtain a white powdery solid, which is [$^{14/15}$N]-L-citrulline with a purity of 99.9% or more.

The isotope-labeled [$^{14/15}$N]-L-citrulline provided in the present application provides an effective approach for the diagnosis and treatment of prostate diseases, CVDs, and the like.

DETAILED DESCRIPTION OF THE EMBODIMENTS

The present application will be described in detail below with reference to examples, but the present application is not limited to these examples.

Unless otherwise specified, the raw materials in the examples of the present application are purchased from a discovery platform. The plasmid pXMJ19 is purchased from Wuhan Miaoling Biotechnology Co., Ltd.

The *C. glutamicum* ATCC13032 is purchased from Guangdong Microbial Culture Collection Center (GDMCC).

According to an embodiment of the present application, it mainly includes: 1) target genes (cipA and arc) are each chemically synthesized; 2) the synthesized cipA and arc are continuously ligated to the vector pXMG19 to construct an expression vector pXMJ19-cipA-arc; 3) the pXMJ19-cipA-arc is introduced into *C. glutamicum* ATCC13032 through electroporation; 4) induction expression is conducted and the inclusion body cipA-arc (namely, the fusion protein cipA-arc) is isolated; and 5) the inclusion body cipA-arc is used to catalyze the conversion of arginine to produce [$^{14/15}$N]-L-citrulline.

In an embodiment of the present application, a [$^{14/15}$N]-L-citrulline conversion rate is calculated based on a mole number of carbon.

Example 1 Construction of an ADI-Containing Genetically Engineered Strain

According to the cipA gene sequence reported by Kirsten Jung et al. (2016), a coding region DNA optimized according to a codon bias of *C. glutamicum* was chemically synthesized by GENEWIZ. The cipA gene sequence was as follows:

(SEQ ID NO: 1)
ATGATCAACGACATGCACCCATCCCTGATCAAGGACAAGGACATGATGGA

CGACGTTATGCTGCGCTCCTGCAAGATCATCGCTATGAAGATCATGCCAG

ACAAGGTTATGCAGGTTATGGTTACCGTTCTGATGCTGGACGGCACCTCC

GAGGAGATGCTGCTGAAGTGGAACCTGCTGGACAACCGCGGCATGGCTAT

CTACAAGGTTCTGATGGAGGCTCTGTGCGGCAAGAAGGACGTTAAGATCG

GCACCGTTGGCAAGGTTGGCCCACTGGGCTGCGACTACATCAACTGCGTT

GAGATCTCCATG.

A HindIII site was introduced at a 5' terminus of the synthesized gene sequence (SEQ ID NO: 1), a SalI site was introduced at a 3' terminus of the synthesized gene sequence to obtain a target fragment, and the target fragment was sequenced; each of the target fragment and an expression vector pXMJ19 (Biofeng) was subjected to double enzyme digestion with HindIII/SalI, each of enzyme digestion products was recovered by gel, and the target fragment and the vector were ligated; and a ligation product was transformed into *E. coli* DH5α competent cells to obtain a positive transformant, which was named pXMJ19-cipA after identification.

1.2 According to the ADI (arc) gene sequence reported by Kim et al. (2007), a coding region DNA optimized according to a codon bias of *C. glutamicum* was chemically synthesized by GENEWIZ. The arc gene sequence was as follows:

(SEQ ID NO: 2)
ATGAACAACGGCATCAACGTTAACTCCGAGATCGGCAAGCTGAAGTCCGT

TCTGCTGCACCGCCCAGGCGCTGAGGTTGAGAACATCACCCCAGACACCA

TGAAGCAGCTGCTGTTCGACGACATCCCATACCTGAAGATCGCTCAGAAG

GAGCACGACTTCTTCGCTCAGACCCTGCGCGACAACGGCGCTGAGACCGT

TTACATCGAGAACCTGGCTACCGAGGTTTTCGAGAAGTCCTCCGAGACCA

AGGAGGAGTTCCTGTCCCACCTGCTGCACGAGGCTGGCTACCGCCCAGGC

CGCACCTACGACGGCCTGACCGAGTACCTGACCTCCATGTCCACCAAGGA

CATGGTTGAGAAGATCTACGCTGGCGTTCGCAAGAACGAGCTGGACATCA

AGCGCACCGCTCTGTCCGACATGGCTGGCTCCGACGCTGAGAACTACTTC

TACCTGAACCCACTGCCAAACGCTTACTTCACCCGCGACCCACAGGCTTC

CATGGGCGTTGGCATGACCATCAACAAGATGACCTTCCCAGCTCGCCAGC

CAGAGTCCCTGATCACCGAGTACGTTATGGCTAACCACCCACGCTTCAAG

GACACCCCAATCTGGCGCGACCGCAACCACACCACCCGCATCGAGGGCGG

CGACGAGCTGATCCTGAACAAGACCACCGTTGCTATCGGCGTTTCCGAGC

GCACCTCCTCCAAGACCATCCAGAACCTGGCTAAGGAGCTGTTCGCTAAC

CCACTGTCCACCTTCGACACCGTTCTGGCTGTTGAGATCCCACACAACCA

CGCTATGATGCACCTGGACACCGTTTTCACCATGATCAACCACGACCAGT

TCACCGTTTTCCCAGGCATCATGGACGGCGCTGGCAACATCAACGTTTTC

ATCCTGCGCCCAGGCAAGGACGACGAGGTTGAGATCGAGCACCTGACCGA

CCTGAAGGCTGCTCTGAAGAAGGTTCTGAACCTGTCCGAGCTGGACCTGA

TCGAGTGCGGCGCTGGCGACCCAATCGCTGCTCCACGCGAGCAGTGGAAC

GACGGCTCCAACACCCTGGCTATCGCTCCAGGCGAGATCGTTACCTACGA

CCGCAACTACGTTACCGTTGAGCTGCTGAAGGAGCACGGCATCAAGGTTC

ACGAGATCCTGTCCTCCGAGCTGGGCCGCGGCCGCGGCGGCGCTCGCTGC

ATGTCCCAGCCACTGTGGCGCGAGGACCTGTAA.

A XhoI site was introduced at a 5' terminus of the synthesized gene sequence (SEQ ID NO: 2), a SacI site was introduced at a 3' terminus of the synthesized gene sequence to obtain a target fragment, and the target fragment was sequenced; each of the target fragment and an expression vector pXMJ19-cipA was subjected to double enzyme digestion with XhoI/SacI, each of enzyme digestion products was recovered by gel, and the target fragment and the vector were ligated; and a ligation product was transformed into E. coli DH5α competent cells to obtain a positive transformant, which was named pXMJ19-cipA-arc after identification, namely, the ADI-containing genetically engineered strain. The genetically engineered strain had a deposition name of C. glutamicum SUMHS-2020.01; and the genetically engineered strain was deposited in the China General Microbiological Culture Collection Center (CGMCC) of Chinese Academy of Sciences, No. 1, Beichen West Road, Chaoyang District, Beijing, China on Jan. 17, 2020, with a deposit number of CGMCC No. 19404.

Example 2 Expression of the Fusion Protein cipA-Arc 2.1 Preparation of C. glutamicum Competent Cells C. glutamicum ATCC13032 was streaked on an LBG-containing solid medium plate and cultivated in a 30° C. incubator for a period of time; fresh bacteria were picked and inoculated in an LBG liquid medium, and cultivated for 12 h to 24 h in a shaker with a temperature of 30° C. and a rotational speed of 200 r/min; an activated bacterial solution was transferred to an LBG medium at an inoculum amount of 1%, and cultivated in a shaker with a temperature of 30° C. and a rotational speed of 200 r/min until $OD_{600}$ was about 0.9; a resulting bacterial solution was pre-cooled for 15 min to 20 min in an ice/water mixture, then dispensed into sterilized 50 mL centrifuge tubes in a clean bench, centrifuged at 6,000 g and 4° C. for 30 s, and placed in ice water for 2 min; a resulting supernatant in each centrifuge tube was discarded, 2.5 mL of pre-cooled 10% glycerin was immediately added to each centrifuge tube, and a resulting mixture was slowly pipetted up and down with a pipette until bacteria were suspended; a resulting suspension was centrifuged at 6,000 g and 4° C. for 30 s, a resulting supernatant was discarded, 500 μL of pre-cooled 10% glycerin was immediately added, and a resulting mixture was slowly pipetted up and down until the bacteria were suspended; the operation was repeated three times.

2.2 Transformation of the Recombinant Plasmid pXMJ19-cipA-Arc into the Competent Cells Through Electric Shock 80 μL of the competent cells and 2 μL of the recombinant plasmid pXMJ19-cipA-arc were thoroughly mixed, cooled on ice for 10 min, and immediately added to an ice-cold cuvette, and electric shock was conducted for 5 ms at a voltage of 2.5 kV; the cuvette was taken out as soon as possible at the end of a pulse, 1 mL of an LBG liquid medium was added at room temperature, and a resulting mixture was transferred to a centrifuge tube and cultivated at 30° C. under gentle shaking for 2 h; 200 μL of a resulting bacterial solution was coated on a 20 μg/ml chloramphenicol-resistant plate; and single colonies were picked to extract the plasmid, and the insertion of the target fragment was confirmed through double enzyme digestion and PCR.

2.3 Induction Expression of the Genetically Engineered Strain

The recombinant strain identified as positive was inoculated in an LBG medium that included chloramphenicol at a final concentration of 20 μg/mL, and cultivated in a shaker with a temperature of 30° C. and a rotational speed of 200 r/min until an $OD_{600}$ value of a bacterial solution reached 0.9; IPTG was added at a final concentration of 1 mM to induce overnight at a temperature of 30° C. and a rotational speed of 180 r/min, and a resulting bacterial solution was centrifuged at 4° C. to obtain recombinant whole cells; and the recombinant whole cells were washed twice with a 50 mM Tris-HCl buffer at a pH of 7.0, resuspended in 50 mM PBS at a pH of 6.5, subjected to ultrasonic disruption, and centrifuged at 4° C. to obtain a precipitate, which was an inclusion body cipA-arc (namely, the fusion protein cipA-arc).

2.4 Determination of the Activity of the Fusion Protein cipA-Arc by Spectrophotometry The enzymatic activity of the cipA-ADI fusion protein was determined through a specific chromogenic reaction of L-citrulline with diacetylmonoxime in a strongly acidic solution and a linear relationship between an absorbance of a reaction complex at 490 nm and a concentration of L-citrulline. A substrate solution (pH 6.0, 50 mM PBS) with [$^{14/15}$N]-L-arginine at a final concentration of 200 mM was prepared. 2.8 mL of the substrate solution was taken, 0.2 mL of an enzyme solution was added, and a reaction was conducted at 37° C. for 10 min. An enzyme reaction solution was diluted appropriately (10 to 100 times). 2 mL of a diluted reaction solution was taken, 3 mL of a mixed acid (volume ratio: $H_2SO_4:H_3PO_4=1:3$) solution was added, and 0.5 mL of a mixture of diacetylmonoxime and thiosemicarbazide was added; and a resulting mixture was thoroughly shaken and immediately placed in a boiling water bath for 10 min, and then an absorbance at 530 nm was determined. Definition of the enzymatic activity of the cipA-ADI fusion protein: at 37° C. and pH 6.0, an enzyme amount required to catalyze the conversion of $[^{14/15}N]$-L-arginine into 1 μmol of citrulline per minute was defined as one unit for enzyme activity (1U). Definition of specific enzyme activity: the number of units for enzyme activity included in per mg of protein (U/mg). A protein concentration was determined by the Bradford method.

Example 3 Expression of the Fusion Protein cipA-Arc

The experimental conditions and steps were the same as those in Example 2, except that the cultivation in step 2.1 was conducted at a temperature of 20° C. and a rotational speed of 300 r/min until $OD_{600}$ was about 0.3.

Example 4 Expression of the Fusion Protein cipA-Arc

The experimental conditions and steps were the same as those in Example 2, except that the cultivation in step 2.1 was conducted at a temperature of 37° C. and a rotational speed of 150 r/min until $OD_{600}$ was about 1.0.

Example 5 Expression of the Fusion Protein cipA-Arc

The experimental conditions and steps were the same as those in Example 2, except that the cultivation in step 2.1 was conducted at a temperature of 40° C. and a rotational speed of 180 r/min until $OD_{600}$ was about 0.72.

Influence of different implementation conditions on the preparation of *C. glutamicum* competent cells

| Example | Cultivation temperature (° C.) | Rotational speed (r/min) | $OD_{600}$ | Number of competent cells |
|---|---|---|---|---|
| Example 2-2.1 | 30 | 200 | 0.9 | Normal |
| Example 3 | 20 | 300 | 0.3 | Small |
| Example 4 | 37 | 150 | 1.0 | Normal |
| Example 5 | 40 | 180 | 0.72 | Small |

Example 6 Expression of the Fusion Protein cipA-Arc

The experimental conditions and steps were the same as those in Example 2, except that the electric shock in step 2.2 was conducted for 10 ms at a voltage of 1 kV.

Example 7 Expression of the Fusion Protein cipA-Arc

The experimental conditions and steps were the same as those in Example 2, except that the electric shock in step 2.2 was conducted for 1 ms at a voltage of 5 kV.

Influence of different electric shock conditions on the conversion efficiency of *C. glutamicum* competent cells

| Example | Voltage of electric shock (kV) | Time of electric shock (ms) | Cultivation temperature (° C.) | Number of successfully-transformed recombinant single colonies |
|---|---|---|---|---|
| Example 2-2.2 | 2.5 | 5 | 37 | 200 |
| Example 6 | 1 | 10 | 37 | 53 |
| Example 7 | 5 | 1 | 37 | 12 |

Example 8 Expression of the Fusion Protein cipA-Arc

The experimental conditions and steps were the same as those in Example 2, except that, in step 2.3, the cultivation was conducted at a temperature of 40° C. and a rotational speed of 150 r/min until $OD_{600}$ was about 0.7; and the induction was conducted at a temperature of 40° C. and a rotational speed of 150 r/min.

Example 9 Expression of the Fusion Protein cipA-Arc

The experimental conditions and steps were the same as those in Example 2, except that, in step 2.3, the cultivation was conducted at a temperature of 20° C. and a rotational speed of 300 r/min until $OD_{600}$ was about 0.5; and the induction was conducted at a temperature of 20° C. and a rotational speed of 200 r/min.

Example 10 Expression of the Fusion Protein cipA-Arc

The experimental conditions and steps were the same as those in Example 2, except that, in step 2.3, the cultivation was conducted at a temperature of 25° C. and a rotational speed of 150 r/min until $OD_{600}$ was about 1.0; and the induction was conducted at a temperature of 35° C. and a rotational speed of 220 r/min.

Influence of different cultivation conditions on the expresssion efficiency of the fusion protein cipA-arc in the recombinant *C. glutamicum*

| Example | Cultivation temperature (° C.) | Rotational speed (r/min) | $OD_{600}$ | Inducer concentration (mM) | Temperature during induction (° C.) | Rotational speed during induction (r/min) | cipA-arc Specific activity (U/mg) |
|---|---|---|---|---|---|---|---|
| Example 2-2.3 | 30 | 200 | 0.9 | 1 | 30 | 180 | 23.1 |
| Example 8 | 40 | 250 | 0.7 | 1 | 40 | 150 | 22.5 |

| | | | | | Rotational | cipA- |
| | Cultivation | Rotational | | Inducer | Temperature | speed | arc |
| | temperature | speed | | concentration | during | during | Specific |
| | | | | | induction | induction | activity |
| Example | (° C.) | (r/min) | OD$_{600}$ | (mM) | (° C.) | (r/min) | (U/mg) |
|---|---|---|---|---|---|---|---|
| Example 9 | 20 | 300 | 0.5 | 1 | 20 | 200 | 21.8 |
| Example 10 | 25 | 150 | 1.0 | 1 | 35 | 220 | 22.9 |

Influence of different cultivation conditions on the expresssion efficiency of the fusion protein cipA-arc in the recombinant *C. glutamicum*

Example 11 Conversion of [$^{14/15}$N]-L-Arginine to Produce [$^{14/15}$N]-L-Citrulline

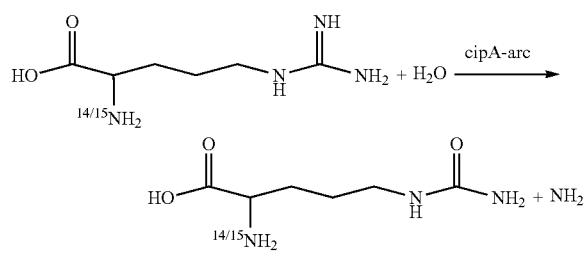

The inclusion body cipA-arc, namely, the fusion protein cipA-arc (9,200U), was added to 1 L of a conversion solution, and a conversion reaction was conducted at 37° C. for 5 h, where the conversion solution included 400 g of [$^{14/15}$N]-L-arginine as a substrate and had a pH of 6.5. A conversion rate of [$^{14/15}$N]-L-arginine was 99.9% or more.

A resulting reaction mixture was centrifuged to obtain a supernatant and a precipitate; the supernatant was subjected to vacuum concentration, crystallization, filtration, and drying to obtain 389.6 g of a white powdery solid, with a yield of 97.4%, which was [$^{14/15}$N]-L-citrulline with a purity of 99.9% or more; and the precipitate was resuspended in 50 mM PBS with a pH of 6.5, and then added to the conversion solution for conversion. The reaction was repeated 50 times, at which point the enzymatic activity was reduced by 1.5%, and an unused enzyme was added in proportion or the used enzyme was partly replaced by the unused enzyme.

Example 12 Conversion of [$^{14/15}$N]-L-Arginine to Produce [$^{14/15}$N]-L-Citrulline The experimental conditions and steps were the same as those in Example 11, except that the conversion reaction was conducted at 25° C. for 8 h; the conversion solution had a pH of 5.0; a conversion rate of [$^{14/15}$N]-L-arginine was 97.6%; 390.8 g of a white powdery solid was obtained, with a yield of 97.7%, which was [$^{14/15}$N]-L-citrulline with a purity of 98.5% or more; and the reaction was repeated 50 times, at which point the enzymatic activity was reduced by 7.6%, an unused enzyme was added in proportion or the used enzyme was partly replaced by an unused enzyme, and the pH was adjusted to 5.0.

Example 13 Conversion of [$^{14/15}$N]-L-Arginine to Produce [$^{14/15}$N]-L-Citrulline The experimental conditions and steps were the same as those in Example 11, except that the conversion reaction was conducted at 50° C. for 2 h; the conversion solution had a pH of 8.0; a conversion rate of [$^{14/15}$N]-L-arginine was 86.5%; 346.0 g of a white powdery solid was obtained, with a yield of 88.3%, which was [$^{14/15}$N]-L-citrulline with a purity of 97.8% or more; and the reaction was repeated 45 times, at which point the enzymatic activity was reduced by 15.4%, an unused enzyme was added in proportion or the used enzyme was partly replaced by an unused enzyme, and the pH was adjusted to 8.0.

Influence of different catalytic conditions on the catalytic efficiency of the fusion protein cipA-arc

| Example | Catalytic temperature (° C.) | pH | Catalytic time (h) | Conversion rate (%) | Number of cycles | Remaining enzymatic activity (%) | Yield (%) | Purity (%) |
|---|---|---|---|---|---|---|---|---|
| Example 11 | 37 | 6.5 | 5 | 99.9 | 50 | 98.5 | 97.4 | 99.9 |
| Example 12 | 25 | 5.0 | 8 | 97.6 | 50 | 92.4 | 97.7 | 98.5 |
| Example 13 | 50 | 8.0 | 2 | 86.5 | 45 | 84.6 | 88.3 | 97.8 |

Example 14 Conversion of [$^{14/15}$N]-L-Arginine to Produce [$^{14/15}$N]-L-Citrulline by Bacterial Whole Cells A 30 g/L genetically engineered strain with the induction expression of the inclusion body cipA-arc was added to 1 L of a conversion solution, and a conversion reaction was conducted at 40° C. for 7 h, where the conversion solution included 400 g of [$^{14/15}$N]-L-arginine as a substrate and had a pH of 6.7. A conversion rate of [$^{14/15}$N]-L-arginine was 99.9% or more. A resulting reaction mixture was centrifuged to obtain a supernatant and a precipitate; the supernatant was subjected to vacuum concentration, crystallization, filtration, and drying to obtain 382.8 g of a white powdery solid, with a yield of 95.7%, which was [$^{14/15}$N]-L-citrulline with a purity of 99.5% or more; the precipitate was resuspended in 50 mM PBS with a pH of 6.7, and then added to the conversion solution for conversion. The reaction was repeated 50 times, at which point the enzymatic activity was reduced by 2.2%, and fresh bacteria were added in proportion or the bacteria in use were partly replaced by fresh bacteria.

Example 15 Conversion of [$^{14/15}$N]-L-Arginine to Produce [$^{14/15}$N]-L-Citrulline The experimental conditions and steps were the same as those in Example 14, except that a 60 g/L genetically engineered strain with the induction expression of the inclusion body cipA-arc was adopted; the conversion reaction was conducted at 37° C. for 3.5 h; the conversion solution had a pH of 6.2; a conversion rate of [$^{14/15}$N]-L-arginine was 99.9% or more; 385.2 g of a white powdery solid was obtained, with a yield of 96.3%, which was [$^{14/15}$N]-L-citrulline with a purity of 99.8% or more; the reaction was repeated 50 times, at which point the enzymatic activity was reduced by 1.6%, fresh bacteria were added in proportion or the bacteria in use were partly replaced by fresh bacteria, and the pH was adjusted to 6.2.

Example 16 Conversion of [$^{14/15}$N]-L-Arginine to Produce [$^{14/15}$N]-L-Citrulline The experimental conditions and steps were the same as those in Example 14, except that a 60 g/L genetically engineered strain with the induction expression of the inclusion body cipA-arc was adopted; the conversion reaction was conducted at 50° C. for 2 b; the conversion solution had a pH of 8.0; a conversion rate of [$^{14/15}$N]-L-arginine was 85.5% or more; 345.2 g of a white powdery solid was obtained, with a yield of 86.3%, which was [$^{14/15}$N]-L-citrulline with a purity of 94.2% or more; the reaction was repeated 45 times, at which point the enzymatic activity was reduced by 7.4%, fresh bacteria were added in proportion or the bacteria in use were partly replaced by fresh bacteria, and the pH was adjusted to 8.0.

| Influence of different catalytic conditions on the catalytic efficiency of the bacterial whole cells including the fusion protein cipA-arc | | | | | | | |
|---|---|---|---|---|---|---|---|
| Example | Catalytic temperature (° C.) | pH | Catalytic time (h) | Conversion rate (%) | Number of cycles | Remaining activity (%) | Yield (%) | Punty (%) |
| Example 14 | 40 | 6.7 | 7 | >99.9 | 50 | 97.8 | 95.7 | 99.5 |
| Example 15 | 37 | 6.3 | 3.5 | >99.9 | 50 | 98.4 | 96.3 | 99.8 |
| Example 16 | 50 | 8.0 | 2 | 85.5 | 45 | 92.6 | 86.3 | 94.2 |

The above examples are merely few examples of the present application, and do not limit the present application in any form. Although the present application is disclosed as above with preferred examples, the present application is not limited thereto. Some changes or modifications made by any technical personnel familiar with the profession using the technical content disclosed above without departing from the scope of the technical solutions of the present application are equivalent to equivalent implementation cases and fall within the scope of the technical solutions.

What is claimed is:

1. A fusion protein cipA-arc, wherein arginine deiminase (ADI) arc is immobilized on a protein crystalline inclusion of cipA to produce cipA-arc with a catalytic activity, wherein the fusion protein cipA-arc comprises the sequence encoded by SEQ ID NO: 1 and the sequence encoded by SEQ ID NO: 2, and wherein the sequences encoded by SEQ ID NO: 1 and SEQ ID NO: 2 are linked by a sequence comprising SalI and XhoI restriction enzyme cleavage sites.

2. A fusion protein cipA-arc, wherein arginine deiminase (ADI) arc is immobilized on a protein crystalline inclusion of cipA to produce cipA-arc with a catalytic activity, wherein
   a specific activity of the cipA-arc is between 21.8 and 23.1 U/mg, wherein the definition of the specific activity is one unit of enzyme activity (1U) required to catalyze the conversion of $[^{14/15}N]$-L-arginine into 1 μmol of citrulline per minute at 37° C. and pH 6.0;
   the catalytic activity catalyzes a conversion reaction of $[^{14/15}N]$-L-arginine to produce $[^{14/15}N]$-L-citrulline and the conversion reaction conducted at 37° C., pH of 6.5 for 5 h has a yield of 97.4% $[^{14/15}N]$-L-citrulline; and
   the fusion protein cipA-arc can catalyze the conversion reaction for 50 times without a reduction in enzymatic activity more than 1.5%; and wherein the fusion protein cipA-arc is prepared by a method comprising the following steps:
(1) preparing C. glutamicum competent cells;
(2) transforming a recombinant plasmid pXMJ19-cipA-arc into the C. glutamicum competent cells prepared in step (1) through electric shock to obtain a genetically engineered recombinant strain, wherein the recombinant plasmid pXMJ19-cipA-arc is constructed by the following process:
(a) obtaining a first target fragment comprising the gene sequence of SEQ ID NO: 1, and sequencing the first target fragment; subjecting each of the first target fragment and an expression vector pXMJ19 to double enzyme digestion using a HindIII restriction enzyme site at the 5' terminus relative to SEQ ID NO: 1 and a SalI restriction enzyme site at the 3' terminus relative to SEQ ID NO: 1, recovering each of enzyme digestion products by gel, and ligating the first target fragment and the expression vector pXMJ19; and transforming a ligation product into Escherichia coli (E. coli) DH5α competent cells to obtain a positive transformant expressing a vector pXMJ19-cipA; and
(b) obtaining a second target fragment comprising the gene sequence of SEQ ID NO: 2, and sequencing the second target fragment; subjecting each of the second target fragment and the vector pXMJ19-cipA to double enzyme digestion using a XhoI restriction enzyme site at the 5' terminus relative to SEQ ID NO: 2 and a SacI restriction enzyme site at the 3' terminus relative to SEQ ID NO: 2, recovering each of enzyme digestion products by gel, and ligating the second target fragment and the vector pXMJ19-cipA; and transforming a ligation product into *E. coli* DH5α competent cells to obtain a recombinant plasmid pXMJ19-cipA-arc; and (3) inducing expression of the fusion protein cipA-arc in the genetically engineered recombinant strain obtained in step (2) by culturing, and subjecting the resulting cells to ultrasonic disruption and centrifugation to obtain a precipitate, wherein the precipitate contains the fusion protein cipA-arc.

3. The fusion protein cipA-arc according to claim 2, wherein in step (1) the preparing *C. glutamicum* competent cells comprises the following:

cultivating *C. glutamicum* ATCC13032 in an Luria-Bertani medium supplemented with 5 g/L glucose (LBG)-containing solid medium, picking and inoculating fresh bacteria in an LBG liquid medium, and cultivating; transferring a resulting bacterial solution to an LBG medium at an inoculum amount of 0.8% to 1.5%, and continuing to cultivate until $OD_{600}$ is 0.8 to 1.0; pre-cooling the resulting bacterial solution by an ice/water mixture, centrifuging, and discarding a resulting supernatant; adding glycerin, and pipetting up and down until bacteria are suspended; centrifuging, and discarding a resulting supernatant; and adding glycerin, and pipetting up and down until bacteria are suspended to obtain the *C. glutamicum* competent cells.

4. The fusion protein cipA-arc according to claim 3, wherein in step (2) the recombinant plasmid pXMJ19-cipA-arc is transformed into the *C. glutamicum* competent cells through the electric shock by the following process:

thoroughly mixing the *C. glutamicum* competent cells and the positive transformant recombinant plasmid pXMJ19-cipA-arc, cooling a resulting mixture on ice, and subjecting the resulting mixture to the electric shock for 1 ms to 10 ms at a voltage of 1 kV to 5 kV under a same temperature condition; adding an LBG liquid medium at room temperature, transferring a resulting mixture to a centrifuge tube, and subjecting the resulting mixture to shaking cultivation; coating a resulting bacterial solution on a chloramphenicol-resistant plate, and picking single colonies to extract a plasmid; and confirming an insertion of the second target fragment through the double enzyme digestion and polymerase chain reaction (PCR).

5. The fusion protein cipA-arc according to claim 4, wherein the electric shock is conducted for 5 ms at a voltage of 2.5 kV.

6. The fusion protein cipA-arc according to claim 5, wherein in step (3), the inducing expression of the fusion protein cipA-arc in the genetically engineered recombinant strain comprises:

inoculating the genetically engineered recombinant strain into a chloramphenicol-containing LBG medium, cultivating on a shaker until an $OD_{600}$ value of a bacterial solution reaches 0.8 to 1.0, and adding isopropyl-β-D-thiogalactoside (IPTG) to induce overnight; centrifuging to collect the recombinant whole cells, washing the strain with a Tris-HCl buffer, and resuspending in phosphate buffer saline (PBS); and subjecting the recombinant whole cells to ultrasonic disruption, and centrifuging to obtain the precipitate, wherein the precipitate contains the fusion protein cipA-arc.

7. The fusion protein cipA-arc according to claim 4, wherein in step (3), the inducing expression of the fusion protein cipA-arc in the genetically engineered recombinant strain comprises:

inoculating the genetically engineered recombinant strain into a chloramphenicol-containing LBG medium, cultivating on a shaker until an $OD_{600}$ value of a bacterial solution reaches 0.8 to 1.0, and adding isopropyl-β-D-thiogalactoside (IPTG) to induce overnight; centrifuging to collect the recombinant whole cells, washing the strain with a Tris-HCl buffer, and resuspending in phosphate buffer saline (PBS); and subjecting the recombinant whole cells to ultrasonic disruption, and centrifuging to obtain the precipitate, wherein the precipitate contains the fusion protein cipA-arc.

8. The fusion protein cipA-arc according to claim 2, wherein the fusion protein cipA-arc is expressed in a genetically engineered strain of *Corynebacterium glutamicum* (*C. glutamicum*) deposited in the China General Microbiological Culture Collection Center (CGMCC) of Chinese Academy of Sciences, No. 1, Beichen West Road, Chaoyang District, Beijing, China on Jan. 17, 2020, with a deposition name of *C. glutamicum* SUMHS-2020.01 and a deposit number of CGMCC No. 19404.

9. A method for preparing $[^{14/15}N]$-L-citrulline through enzymatic catalysis, comprising the following step:

adding the fusion protein cipA-arc according to claim 3 to a conversion solution to allow a conversion reaction, wherein the conversion solution comprises $[^{14/15}N]$-L-arginine and a buffer, and the conversion reaction is conducted for 2 hours to 8 hours at a temperature of 25° C. to 50° C. and a pH of 5.0 to 8.0.

10. The method for preparing $[^{14/15}N]$-L-citrulline through enzymatic catalysis according to claim 9, wherein the buffer is PBS; and the conversion reaction is conducted for 5 hours at a temperature of 37° C. and a pH of 6.5.

11. The method for preparing $[^{14/15}N]$-L-citrulline through enzymatic catalysis according to claim 9, wherein the *C. glutamicum* competent cells are prepared by the following process:

cultivating *C. glutamicum* ATCC13032 in an LBG-containing solid medium, picking and inoculating fresh bacteria in an Luria-Bertani medium supplemented with 5 g/L glucose (LBG) liquid medium, and cultivating; transferring an activated bacterial solution to an LBG medium at an inoculum amount of 0.8% to 1.5%, and continuing to cultivate until OD 600 is 0.8 to 1.0; pre-cooling the resulting bacterial solution by an ice/water mixture, centrifuging, and discarding a resulting supernatant; adding glycerin, and pipetting up and down until bacteria are suspended; centrifuging, and discarding a resulting supernatant; and adding glycerin, and pipetting up and down until bacteria are suspended to obtain the *C. glutamicum* competent cells.

12. The method for preparing $[^{14/15}N]$-L-citrulline through enzymatic catalysis according to claim 11, wherein the recombinant plasmid pXMJ19-cipA-arc is transformed into the *C. glutamicum* competent cells through the electric shock by the following process:

thoroughly mixing the *C. glutamicum* competent cells and the positive transformant recombinant plasmid pXMJ19-cipA-arc, cooling a resulting mixture on ice, and subjecting the resulting mixture to the electric shock for 1 ms to 10 ms at a voltage of 1 kV to 5 kV under a same temperature condition; adding an LBG liquid medium at room temperature, transferring a resulting mixture to a centrifuge tube, and subjecting the resulting mixture to shaking cultivation; coating a resulting bacterial solution on a chloramphenicol-resistant plate, and picking single colonies to extract a plasmid; and confirming an insertion of the second target fragment through the double enzyme digestion and polymerase chain reaction (PCR).

13. The method for preparing $[^{14/15}N]$-L-citrulline through enzymatic catalysis according to claim 12, wherein the electric shock is conducted for 5 ms at a voltage of 2.5 kV.

14. A method of preparing $[^{14/15}N]$-L-citrulline comprising the step of adding the fusion protein cipA-arc according to claim 2 to a conversion solution to allow a conversion reaction.

15. A method of preparing $[^{14/15}N]$-L-citrulline comprising the step of adding the fusion protein cipA-arc according to claim 3 to a conversion solution to allow a conversion reaction.

16. A method of preparing $[^{14/15}N]$-L-citrulline comprising the step of adding the fusion protein cipA-arc according to claim 4 to a conversion solution to allow a conversion reaction.

17. A method of preparing $[^{14/15}N]$-L-citrulline comprising the step of adding the fusion protein cipA-arc according to claim 5 to a conversion solution to allow a conversion reaction.

* * * * *

SEQUENCE LISTING

```
<160> NUMBER OF SEQ ID NOS: 2

<210> SEQ ID NO 1
<211> LENGTH: 312
<212> TYPE: DNA
<213> ORGANISM: Artificial Sequence
<220> FEATURE:
<223> OTHER INFORMATION: The sequence is synthesized.

<400> SEQUENCE: 1
atgatcaacg acatgcaccc atccctgatc aaggacaagg acatgatgga cgacgttatg      60
ctgcgctcct gcaagatcat cgctatgaag atcatgccag acaaggttat gcaggttatg     120
gttaccgttc tgatgctgga cggcacctcc gaggagatgc tgctgaagtg gaacctgctg     180
gacaaccgcg gcatggctat ctacaaggtt ctgatggagg ctctgtgcgg caagaaggac     240
gttaagatcg gcaccgttgg caaggttggc ccactgggct gcgactacat caactgcgtt     300
gagatctcca tg                                                         312

<210> SEQ ID NO 2
<211> LENGTH: 1233
```

<212> TYPE: DNA
<213> ORGANISM: Artificial Sequence
<220> FEATURE:
<223> OTHER INFORMATION: The sequence is synthesized.

<400> SEQUENCE: 2

```
atgaacaacg gcatcaacgt taactccgag atcggcaagc tgaagtccgt tctgctgcac      60
cgcccaggcg ctgaggttga aacatcacc ccagacacca tgaagcagct gctgttcgac     120
gacatcccat acctgaagat cgctcagaag gagcacgact tcttcgctca gaccctgcgc     180
gacaacggcg ctgagaccgt ttacatcgag aacctggcta ccgaggtttt cgagaagtcc     240
tccgagacca aggaggagtt cctgtcccac ctgctgcacg aggctggcta ccgcccaggc     300
cgcacctacg acggcctgac cgagtacctg acctccatgt ccaccaagga catggttgag     360
aagatctacg ctggcgttcg caagaacgag ctggacatca agcgcaccgc tctgtccgac     420
atggctggct ccgacgctga gaactacttc tacctgaacc cactgccaaa cgcttacttc     480
acccgcgacc cacaggcttc catgggcgtt ggcatgacca tcaacaagat gaccttccca     540
gctcgccagc cagagtccct gatcaccgag tacgttatgg ctaaccaccc acgcttcaag     600
gacaccccaa tctggcgcga ccgcaaccac accaccccgca tcgagggcgg cgacgagctg     660
atcctgaaca agaccaccgt tgctatcggc gtttccgagc gcacctcctc caagaccatc     720
cagaacctgg ctaaggagct gttcgctaac ccactgtcca ccttcgacac cgttctggct     780
gttgagatcc cacacaacca cgctatgatg cacctggaca ccgttttcac catgatcaac     840
cacgaccagt tcaccgtttt cccaggcatc atggacggcg ctgcaacat caacgttttc     900
atcctgcgcc caggcaagga cgacgaggtt gagatcgagc acctgaccga cctgaaggct     960
gctctgaaga aggttctgaa cctgtccgag ctggacctga tcgagtgcgg cgctggcgac    1020
ccaatcgctg ctccacgcga gcagtggaac gacggctcca cacccctggc tatcgctcca    1080
ggcgagatcg ttacctacga ccgcaactac gttaccgttg agctgctgaa ggagcacggc    1140
atcaaggttc acgagatcct gtcctccgag ctgggccgcg gccgcggcgg cgctcgctgc    1200
atgtcccagc cactgtggcg cgaggacctg taa                                 1233
```